(12) United States Patent
Langenbach et al.

(10) Patent No.: US 6,726,711 B1
(45) Date of Patent: Apr. 27, 2004

(54) ARTIFICIAL BLOOD VESSEL WITH TRANSCUTANEOUS ACCESS PORTS

(75) Inventors: George Langenbach, Crestwood, MO (US); John G. Robinson, Crestwood, MO (US)

(73) Assignee: Joan L. Robinson, Crestwood, MO (US)

(*) Notice: Subject to any disclaimer, the term of this patent is extended or adjusted under 35 U.S.C. 154(b) by 0 days.

(21) Appl. No.: 10/286,222

(22) Filed: Nov. 1, 2002

(51) Int. Cl.[7] .................................................. A61F 2/06
(52) U.S. Cl. .......................... 623/1.1; 623/11; 604/27; 604/288.01; 604/175; 604/246; 604/245
(58) Field of Search ................... 623/1.1, 11; 604/6.16, 604/7, 8, 9, 288.01–288.04, 19, 27, 174, 104, 246, 247, 249, 256, 587, 890.1, 905

(56) References Cited

U.S. PATENT DOCUMENTS 3,783,868 A * 1/1974 Bokros .................... 604/891.1
4,108,173 A * 8/1978 Slivenko et al. ............ 604/175
4,496,349 A * 1/1985 Cosentino .................. 604/175
4,496,350 A * 1/1985 Cosentino .................. 604/175

* cited by examiner

Primary Examiner—Corrine McDermott
Assistant Examiner—Kamrin Landrem
(74) Attorney, Agent, or Firm—Polster, Lieder, Woodruff & Lucchesi, L.C.

(57) ABSTRACT

A artificial blood vessel for facilitating the introduction of fluids into or withdrawal of fluids from the vascular system of an individual, or both, includes a tubular portion that lies beneath skin of the individual and is grafted to a natural blood vessel. Located along the tubular portion where it is offset laterally from the tubular portion is at least one pocket which encloses a chamber that communicates with the lumen of the tubular portion. The artificial blood vessel also includes a port which is attached to the pocket and has grommet that lies over the skin and contains access bore. The port also has a valve which lies at the end of the access bore to normally prevent blood from escaping through the access bore, but does allow access to the chamber for medical procedures.

20 Claims, 3 Drawing Sheets

ARTIFICIAL BLOOD VESSEL WITH TRANSCUTANEOUS ACCESS PORTS

CROSS REFERANCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

The present invention relates to transcutaneous devices and more particularly to an artificial blood vessel that facilitates access to a vascular system, as well as to a port for a blood vessel.

Those whose kidneys have failed may still lead relatively normal lives by undergoing hemodialysis, perhaps three or four times per week. The procedure involves inserting two catheters into accessible blood vessels—one to withdraw blood and the other reintroduce the blood after it has been cleansed. But natural blood vessels cannot sustain repeated penetrations by catheters without collapsing. Typically, a patient who requires hemodialysis undergoes a surgical procedure in which an artificial blood vessel is grafted onto an artery and a vein in the patient's arm to serve as the shunt. Being formed from a polymer, the artificial blood vessel can withstand repeated penetrations by catheters. Even so, the artificial vessel lies beneath the skin, and with dialysis two catheters must penetrate the skin before entering the artificial blood vessel. The penetrations are extremely painful and may produce infections.

BRIEF SUMMARY OF THE INVENTION

The present invention resides in an artificial blood vessel including a tubular portion, at least one pocket located along the tubular portion where it encloses a chamber that communicates with the interior of the tubular portion. The blood vessel also includes a port at the pocket, with the port having a grommet that is above the pocket and a valve that normally prevents communication between an access opening in the grommet and the chamber in the pocket. The invention also resides in the artificial blood vessel implanted in an individual with its ends grafted to a natural blood vessel. In addition the invention resides in a port having a grommet designed to be located over and through the skin and a valve element beneath the skin.

DETAILED DESCRIPTION OF THE INVENTION

Figure 1:
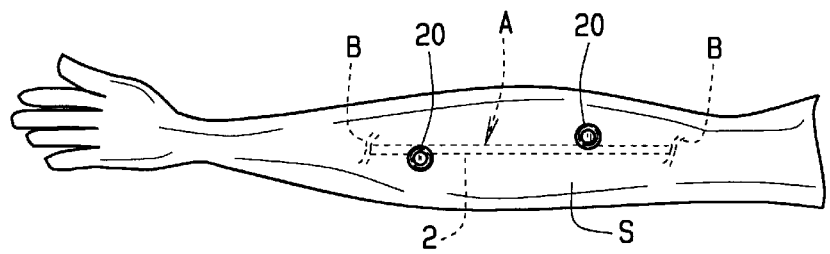
FIG. 1 illustrates a human arm having the artificial blood vessel of the present invention implanted in it and the ports for the vessel exposed at the surface of the skin.

Referring now to the drawings, an individual, who requires hemodialysis or some other medical treatment that necessitates introducing fluids into or withdrawing fluids from the individual's vascular system or both, has (FIG. 1) an artificial blood vessel A located beneath the skin S of that individual at a location that is easily accessible such as in an arm. The artificial blood vessel A actually represents a shunt between an artery and a vein, which are natural blood vessels B. A portion of the artificial blood vessel A opens through the skin S so that one gains access to the vascular system without puncturing the skin S.

Figure 2:
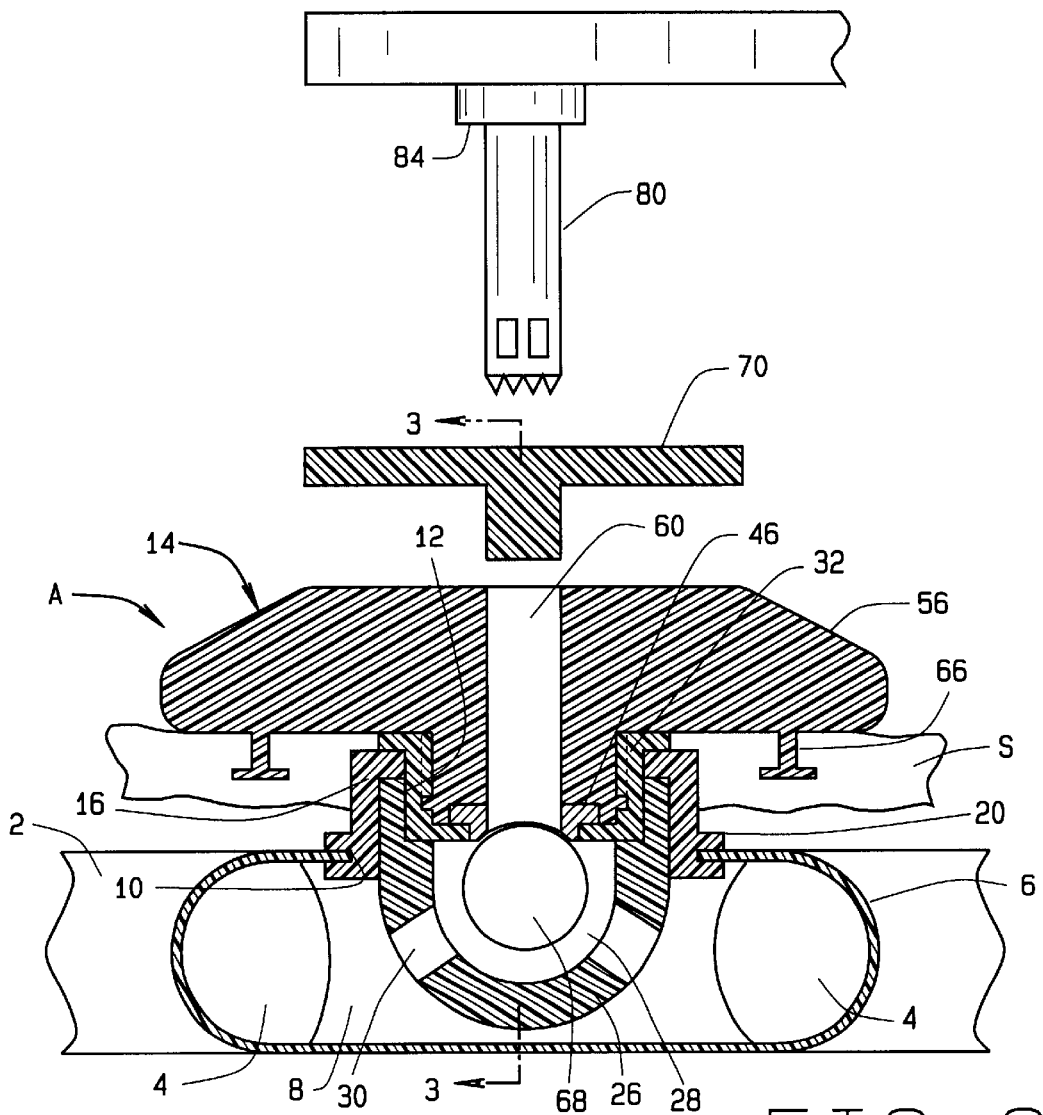
FIG. 2 is a sectional view of the artificial blood vessel at one of its ports.
Figure 3:
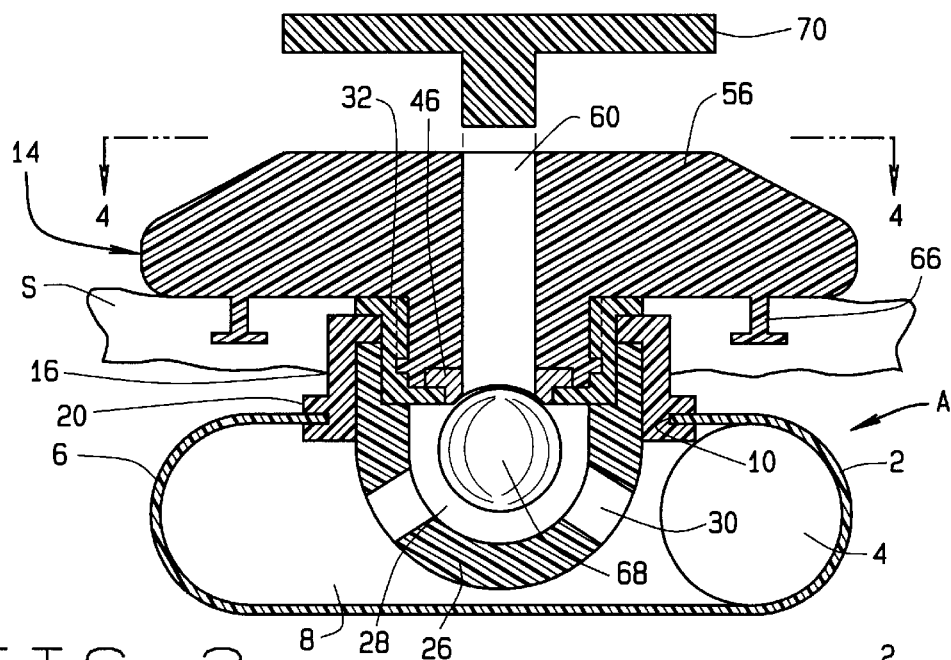
FIG. 3 is a sectional view taken along line 3—3 of FIG. 2.
Figure 4:
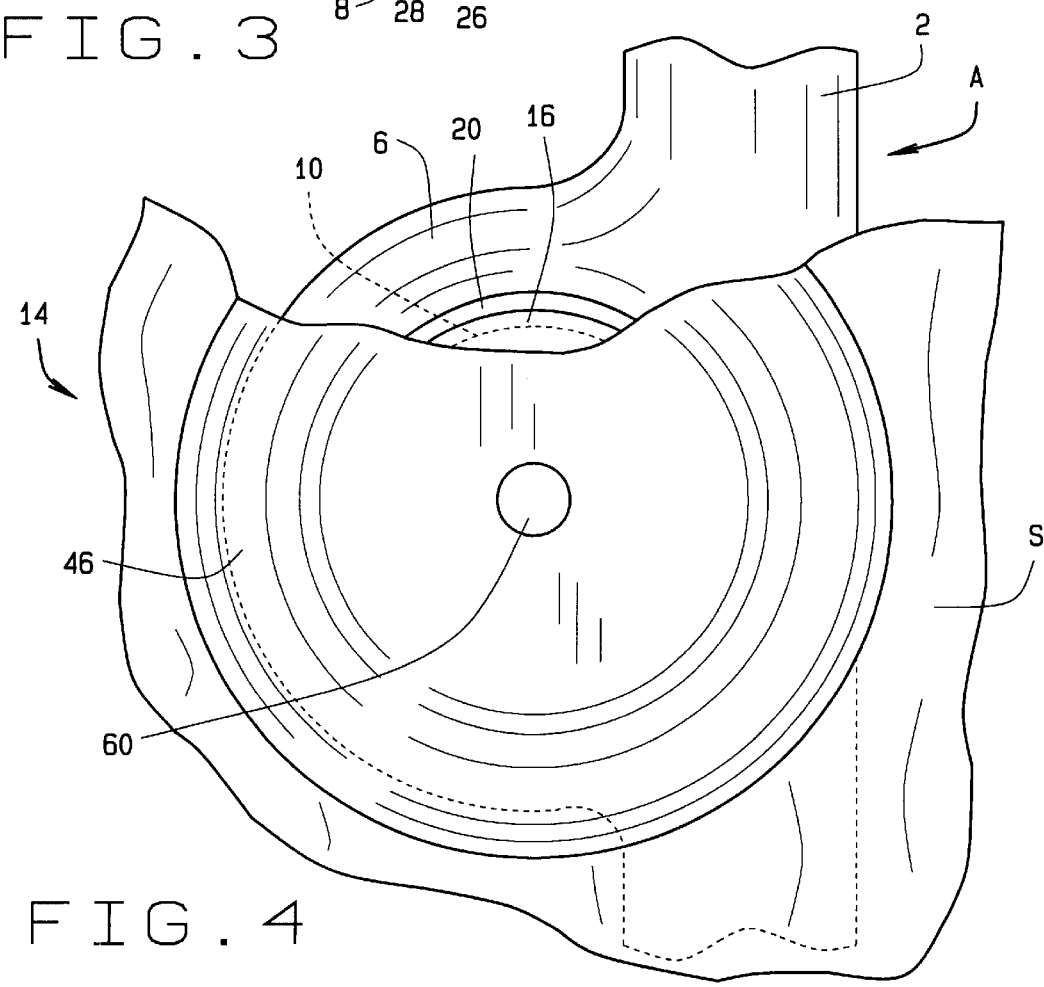
FIG. 4 is a plan view of the artificial blood vessel at one of the ports and taken along line 4—4 of FIG. 3 with the skin broken away to show the underlying pocket and tubular portion.

The artificial blood vessel A, includes (FIGS. 2–4) a tubular portion 2 which is formed from a substance that is flexible and compatible with the body in the sense that it is not toxic and the natural vessels B will graft onto it. One suitable material is a polymer sold under the trademark GORE-TEX by W. L. Gore & Associates, Inc., of Newark, Del. Throughout its length the tubular portion 2 has a hollow interior or lumen 4 which is unobstructed and unrestricted. In addition, the vessel A has at least one pocket 6. For some medical procedures, particularly hemodialysis, the vessel A will have two pockets 6. Each pocket 6 is attached to the tubular portion 2, but is offset laterally and encloses a chamber 8, which at its side opens into the lumen 4 of the tubular portion 2. At its upper end the pocket 6 has a circular opening 10 which is offset generally to the side of the tubular portion 2. Preferably, the tubular portion 2 and the pocket 6 are formed integral and from the same flexible polymer.

In addition to the tubular portion 2 and its pockets 6, the artificial blood vessel A has (FIGS. 2–4) a port 14 for each of its pockets 6. Each port 14 occupies the circular opening 10 for its pocket 6 and further projects downwardly into the pocket 6 and upwardly through the skin S. In that sense the port 14 and the blood vessel A of which it is a part is transcutaneous. The port 14 provides access to the chamber 8 over which it resides and of course to the lumen 4 of the tubular portion 2 without actually puncturing the skin S. For the most part, the port 14 is formed from components that are molded from a polymer that is nontoxic to the individual's body. In comparison to the material of the tubular portion 2 and pockets 6, the polymer from which the components of the port 20 are formed is relatively inflexible.

Figure 5:
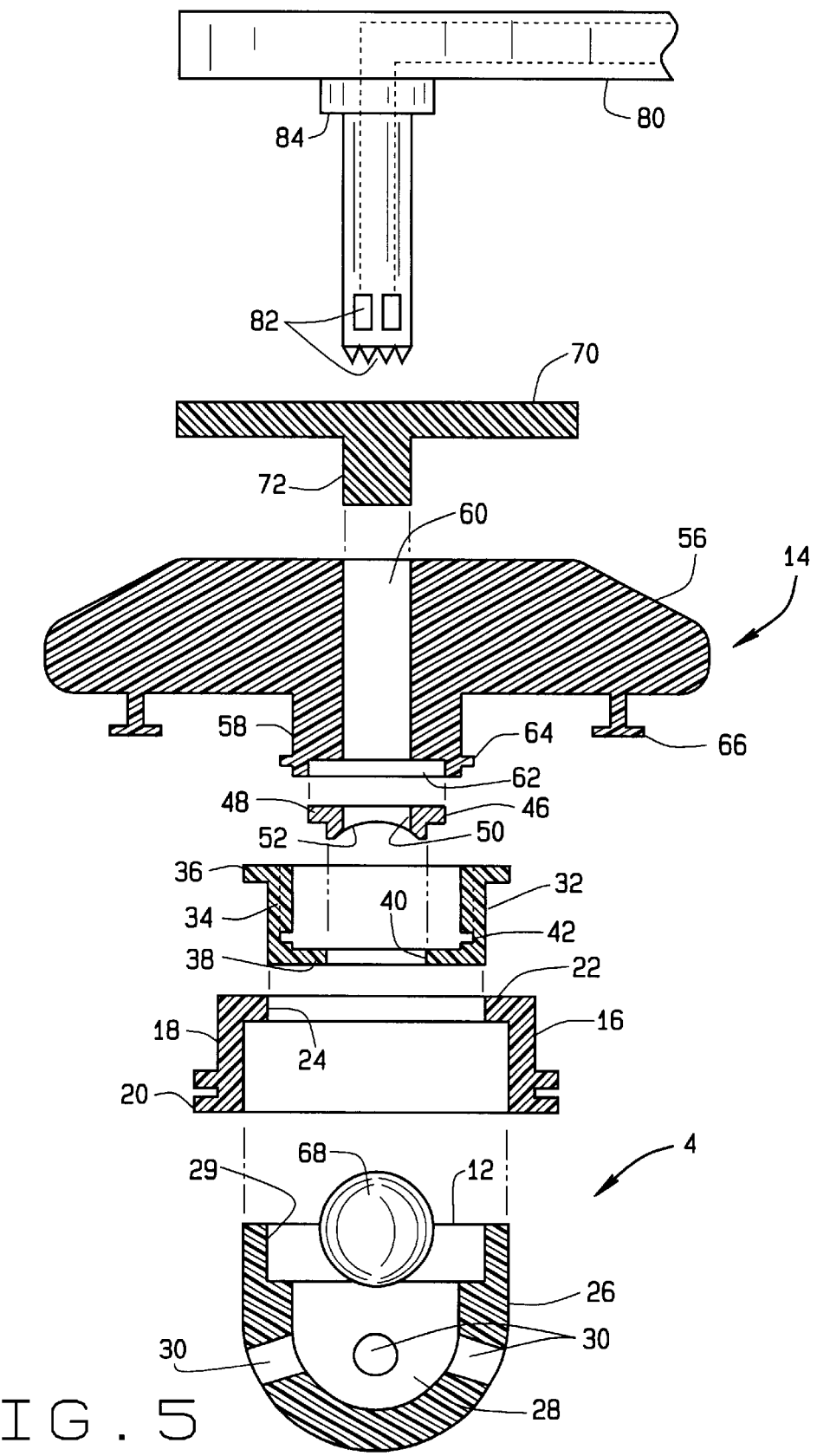
FIG. 5 is an exploded sectional view of one of the ports.

Among the molded components is a rim 16 having (FIGS. 2 & 5) a side wall 18 provided at is lower end with a split rib 20. As such the rib 20 has two circumferential segments separated by a gap. The rim 16 also has an upper wall provided with a circular opening 24. The side wall 18 of the rim 16 fits into the circular opening 10 in the pocket 6. Indeed, the wall of the pocket interlocks with and is bonded to the rim 16 along the split rib 20 of the rim 16 in that a portion of that wall extends into the gap between the two segments of the rib 20.

In addition, the port 14 includes (FIGS. 2 & 5) a cage 26 which fits snugly into the side wall 18 of the rim 16 from beneath and provides a semispherical cavity 28 and a counterbore 29 above the cavity 28. The cage 26 lies mostly within the chamber 8 of the pocket 6 with substantial clearance on the order of ⅛ in. between the side wall of the cage 26 and the side wall of the pocket 6. The cavity 28 communicates with the chamber 8 of the pocket 6—and thus with the lumen 4 of the tubular portion 2 as well—through several apertures 30 in its wall.

The rim 16 in its circular opening 24 receives (FIGS. 2 & 5) a liner 32 having a side wall 34 that extends into the counterbore 29 of the cage 26. The liner 32 at its upper end has a flange 36 which overlies the upper wall 22 of the rim 16 and at its lower end a bottom wall 38 is provided with a circular aperture 40 that leads into the cavity 28 of the cage 26. Within its side wall 34 the liner 32 is provided with bayonet slots 42. The liner 32 is bonded or otherwise secured to the rim 16 along its flange 34 and to the cage 26 along its side wall The liner 32 holds a valve seat 46 (FIG. 5) which is formed from stainless steel or other substance capable of being attracted by a magnet. The seat 46 extends into the circular aperture 40 of the liner 32 and has a flange 48 which overlies the bottom wall 38 of the liner 32. The seat 46 also contains an aperture in the form of a through bore 50 which extends through it and opens into the cavity 28 of the cage 26 along a spherical sealing surface 52 that lies within a spherical envelope.

Externally of the skin S, the port 14 has a grommet 56 (FIG. 5) provided on its underside with a boss 58 that passes through the skin S and fits into the side wall 34 of the liner 32. Extending through the center of the grommet 56 at its cylindrical boss 58 is an access bore 60 which opens into a shallow counterbore 62 at its lower end. Whereas the boss 58 fits into the side wall 34 of the liner 32 with a slight clearance, counterbore 62 at its lower end receives the flange 48 of the valve seat 46 again with a slight clearance. Moreover the boss 58 has nibs 64 projected laterally from it, and they are configured to align with and fit within the bayonet slots 42 in the liner 32. When the nibs 64 occupy the short circumferentially directed portions that form the ends of the bayonet slots 42, the valve seat 46 is captured between the bottom wall 38 of the liner 32 and the boss 58 of the grommet 56, so the valve seat 46 cannot be displaced. With the grommet 56 is so positioned, the access bore 60 in the grommet 56 aligns with and opens into the through bore 50 in the valve seat 46, so the two bores 50 and 60 form an access passage in the port 14. Finally, the grommet 56 on its underside has several skin anchors 66 arranged circumferentially at 600 intervals. Each anchor 66 includes a thin post extended from the bottom surface of the grommet 56, that is the surface that lies over the skin S, and a disk at the bottom of the post. The skin S grows around the anchors 66 to retain the grommet 56, and indeed the entire port 14, in place on the skin S. In lieu of being formed from a polymer, the grommet 56 may be formed from a nontoxic metal.

The cavity 28 within the cage 26 of the port 14 contains a ball 68 (FIGS. 2 & 3) having essentially the same radius as the radius of the sealing surface 52 on the valve seat 46. Moreover, the ball 68 is formed from a substance, that is magnetized so that the magnetic force attracts it to the valve seat 46. Indeed, the ball 68 forms a valve element which, owing to the magnetic attraction, normally remains against the sealing surface 52 on the valve seat 46, thus blocking the access bore 60 in the grommet 56 so that blood which flows through the lumen 4 in the tubular portion 2 will not escape at the port 20. The ball 68 may also be biased against the valve seat 46 with a spring located between it and the bottom surface of the cage 26. The valve seat 46 and ball 68 form a valve within the port 14.

Finally, the port 14 has a removable closure 70 (FIG. 5) which fits over the grommet 58 and is provided with a cylindrical plug 72 that fits into the access bore 60 to prevent contaminants from entering it. The closure 70 is easily removed from the grommet 56 to expose the access bore 60.

To implant the artificial blood vessel A in a patient requires a minor surgical procedure in which an incision is made in the patient's arm near an artery and a vein, both natural blood vessels B (FIG. 1). The ends of the tubular portion 2 are connected to the artery and to the vein such that grafts develop at those ends. While the surgical procedure implants the entire tubular portion 2 and pockets 6 as well as much of the ports 14 into the patient's body, although close to the skin, the grommets 56 for the ports 14 remain above the skin S. In time the incision, through healing, closes, and the skin S grows around the side wall 26 of the rim 16 for each port 14 and also around the anchors 66 on the grommet 56.

Once the artificial blood vessel A is implanted in the patient's body and the incision has healed and the grafts taken, the artificial blood vessel A is available for introducing fluids into patient's vascular system or withdrawing fluids from the system or both, depending on the number of ports 14 in the vessel A. To do so requires a cannula 80 (FIG. 5) which is small enough in diameter to fit into the access bore 60 of the grommet 56. At its end, the cannula 80 has openings 82 through which the hollow interior of the cannula 80 is exposed. In addition, the cannula 80 has a shoulder 84 which is too large to fit into the access bore 60 and is spaced a prescribed distance from the end at which the openings 82 are located. That distance is great enough to enable the cannula 80 to unseat the ball 68 from the seat 50 before the shoulder 84 bottoms out against the grommet 56, but is not great enough to enable the cannular 80 to drive the ball 68 against the cage 26. In other words, the shoulder 84 encounters the upper surface of the grommet 56 before the ball 68 reaches the bottom of the cage 26. In this condition, the apertures 82 in the cannula 80 are exposed to the cavity 28 in the cage 26. Preferably, the shoulder 84 is formed from an elastomer so that it effects a seal with the surface of the grommet 56 around the outer end of the access bore 60.

The closure 70 is removed from the grommet 56, thus exposing the outer end of the access bore 60, but no blood escapes inasmuch as the ball 68 remains against the sealing surface 52 on the valve seat 46. Next the distal end of the cannula 80 is inserted into the exposed access bore 60 of the grommet 56. It advances through the access bore 60 and eventually encounters the ball 68 that is against the valve seat 46. The cannula 80 displaces the ball 68 from the sealing surface 52 of valve seat 46 and enters the cavity 28 of the cage 26 far enough to expose the openings 82 in its distal end to the cavity 28. As it does, the shoulder 84 comes against the surface of the grommet 56 and establishes a seal around the outer end of the access bore 60. Since the cavity 28 of the cage 26 communicates with the chamber 8 of the pocket 6 through the apertures 30 in the cage 26 and the chamber 8 communicates with the lumen 4 of the tubular portion 2, blood may be withdrawn from the patent's vascular system through the cannula 80 to be cleansed. The treated blood is introduced back into the vascular system through another cannula 80 which is inserted into the other port 14. Upon withdrawal cannula 80 a saline solution should be introduced through the cannula 80 to cleanse the access bore 60 outwardly from the ball 68 and seat 52 as well as the cannula 80. Likewise, pharmaceuticals may be introduced into the patient's vascular system through the cannula 80 and port 14.

When the balls 68 are against their valve seats 46 in the ports 14, blood flows through the tubular portion 2 of the blood vessel A without hindrance, and certainly without hindrance from the pockets 6 and ports 14, inasmuch as the pockets 6 are offset laterally from the tubular portion 2.

The blood vessel A may be implanted in animals other than human beings.

What is claimed is:

1. An artificial blood vessel comprising:
   a tubular portion suitable for implanting beneath the skin of a living animal and being formed from a material to which a natural blood vessel will graft, the tubular portion having a lumen;

a pocket located along the tubular portion and also suitable for implanting beneath the skin of the living animal, the pocket enclosing a chamber which communicates with the lumen of the tubular portion; and a port attached to the pocket and configured to project through the skin of the living animal, the port including a passage which extends through it and opens into the chamber of the pocket, the port also having a sealing surface that surrounds the passage where the passage opens into the chamber, the port also including a valve element which normally bears against the sealing surface to isolate the passage from the chamber of the pocket, but is displaceable away from the sealing surface such that the valve element and sealing surface are separated; thus enabling the passage to communicate with the chamber of the pocket.

2. A blood vessel according to claim 1 wherein the sealing surface lies in a spherical envelope, and the valve element is spherical.

3. A blood vessel according to claim 2 wherein the tubular portion and pocket are formed from a flexible material.

4. An artificial vessel according to claim 1 wherein the pocket is offset with respect to the tubular portion.

5. An artificial blood vessel according to claim 1 wherein the port further includes a cage which is in the chamber of the pocket and encloses a cavity which communicates with the chamber; and wherein the passage opens into the cavity, and the valve element is loosely received in the cavity.

6. An artificial blood vessel according to claim 1 wherein the valve element is biased toward the sealing surface.

7. An artificial blood vessel according to claim 6 wherein the port also includes a valve seat formed from a ferrous metal, with the sealing surface being on the valve seat and the passage extending through the valve seat; and wherein the valve element is magnetized.

8. An artificial blood vessel according to claim 1 wherein the pocket is one of two pockets located along the tubular portion where they are spaced apart, and the port is one of two ports, there being a separate port attached to each pocket; and wherein the valve elements of the two ports are operable independently of each other.

9. An artificial blood vessel comprising: a tubular portion formed from a flexible material and having a lumen; at least one pocket located along the tubular portion and also formed from a flexible material, the pocket being offset to the side of the tubular portion and enclosing a chamber which communicates with the lumen of the tubular portion; and a port attached to the pocket for providing access to the chamber enclosed by the pocket, the port having a grommet provided with passage that leads to the chamber in the pocket, the port including a rim that is attached to the pocket and a liner that is located within the rim and behind the grommet, the port also including a valve for normally isolating the passage from the chamber, but being capable of providing communication between the passage and the chamber.

10. A blood vessel according to claim 9 wherein the grommet includes a cylindrical boss that projects into the liner, and the passage in the grommet extends through the cylindrical boss.

11. A blood vessel according to claim 9 wherein the port further includes a closure which fits into the opening of the grommet remote from the cylindrical boss.

12. An artificial blood vessel comprising: a tubular portion having a lumen; two pockets located along the tubular portion, with each enclosing a chamber which communicates with the lumen of the tubular portion; and a port attached to each pocket for providing access to the chamber enclosed by the pocket, each port having a grommet provided with passage that leads to the chamber of its pocket, each port also including a cage that is in the chamber of the pocket and encloses a cavity that communicates with the chamber of the pocket; each port further including a valve for normally isolating the passage from the chamber, but being capable of providing communication between the passage and the chamber, the valve including a valve seat located at the end of the passage and provided with a sealing surface through which the passage communicates with the cavity in the cage; the valve also including a valve element located in the cavity and having the capacity to move between an open position, wherein it is located away from the sealing surface, and a closed position wherein it is against the sealing surface.

13. For use in the body of a living animal that has skin and a vascular system beneath the skin, with the vascular system including a natural blood vessel, an artificial blood vessel that is capable of being connected to the natural blood vessel, said artificial blood vessel comprising: a tubular portion to be located beneath the skin and having a hollow interior and an end to which the natural blood vessel is capable of being grafted; at least one pocket also to be located beneath the skin and attached to, yet offset laterally from, the tubular portion, the pocket enclosing a chamber which communicates with the hollow interior of the tubular portion; and a port including a grommet to be located over the skin and having a boss for passing through the skin to the pocket, the grommet having an access bore that leads from the exterior surface of the grommet toward the chamber in the pocket, the port further including a liner which extends into the pocket and receives the boss on the grommet, with the boss mechanically engaging the liner, the port having a valve that normally closes the access bore, but is capable if permitting communication between the access bore and the chamber, the valve including a valve seat captured between the liner and the boss and provided with an aperture at the end of and aligned with access bore in the grommet and also a sealing surface around the aperture, and a valve element that moves between a closed position against the sealing surface, wherein it isolates the chamber from the access bore, and an open position, wherein it is separated from the sealing surface.

14. For use in the body of a living animal that has skin and a vascular system beneath the skin, with the vascular system including a natural blood vessel, an artificial blood vessel that is capable of being connected to the natural blood vessel, said artificial blood vessel comprising: a tubular portion to be located beneath the skin and having a hollow interior and an end to which the natural blood vessel is capable of being grafted; at least one pocket also to be located beneath the skin and attached to, yet offset laterally from, the tubular portion, the pocket enclosing a chamber which communicates with the hollow interior of the tubular portion; and a port including a grommet to be located over the skin and having a boss for passing through the skin to the pocket, the grommet having an access bore that leads from the exterior surface of the grommet toward the chamber in the pocket, the port also including a liner which extends into the pocket and receives the boss on the grommet, the port having a valve that normally closes the access bore, but is capable if permitting communication between the access bore and the chamber, the valve including a valve seat provided with an aperture at the end of and aligned with access bore in the grommet and also having a sealing surface around the aperture; the valve also including a valve element is that is biased toward the valve seat and moves between a closed position against the sealing surface, wherein it isolates the chamber from the access bore, and an open position, wherein it is separated from the sealing surface.

15. The artificial blood vessel according to claim 14 wherein the valve seat is formed from a ferrous metal and the ballis magnetized.

16. The artificial blood vessel according to claim 14 wherein the port also includes a cage toward which the sealing surface of the valve seat is presented, with the cage defining a cavity that is in communication with the chamber of the pocket, and within which the valve element is located.

17. For use in the body of a living animal that has skin and a vascular system beneath the skin, with the vascular system including a natural blood vessel, an artificial blood vessel that is capable of being connected to the natural blood vessel, said artificial blood vessel comprising: a tubular portion to be located beneath the skin and having a hollow interior and an end to which the natural blood vessel is capable of being grafted; at least one pocket also to be located beneath the skin and attached to, yet offset laterally from the tubular portion, the pocket enclosing a chamber which communicates with the hollow interior of the tubular portion; and a port including a grommet to be located over the skin and also to be extended through the skin to the pocket, the grommet having an access bore that leads from the exterior surface of the grommet toward the chamber in the pocket, the port having a valve that normally closes the access bore, but is capable of permitting communication between the access bore and the chamber, the valve including a valve seat provided with an aperture at the end of an aligned with access bore in the grommet and also a sealing surface around the aperture the valve also including a valve element that moves between a closed position against the sealing surface, wherein it isolates the chamber from the access bore, and an open position, wherein it is separated from the sealing surface; and a closure fitted into the access bore of the grommet.

18. For use in the body of a living animal that has skin and a vascular system beneath the skin with the vascular system including a natural blood vessel, an artificial blood vessel that is capable of being connected to the natural blood vessel, said artificial blood vessel comprising: a tubular portion to be located beneath the skin and having a hollow interior and an end to which the natural blood vessel is capable of being grafted; at least one pocket also to be located beneath the skin and attached to, yet offset laterally from the tubular portion, the pocket enclosing a chamber which communicates with the hollow interior of the tubular portion; and a port including a grommet to be located over the skin and also extending through the skin to the pocket, the grommet having an access bore that leads from the exterior surface of the grommet toward the chamber in the pocket, the port having a valve that normally closes the access bore, but is capable if permitting communication between the access bore and the chamber, the valve including a valve seat provided with an aperture at the end of and aligned with access bore in the grommet and also a sealing surface around the aperture; and the valve also including a valve element that moves between a closed position against the sealing surface, wherein it isolates the chamber from the access bore, and an open position, wherein it is separated from the sealing surface; and a cannula located in the access bore at the grommet and projecting into the valve seat sufficiently to displace the valve element from the sealing surface.

19. For use in the body of a living animal that has skin and a vascular system beneath the skin, with the vascular system including a natural blood vessel, an artificial blood vessel that is capable of being connected to the natural blood vessel, said artificial blood vessel comprising: a tubular portion to be located beneath the skin and having a hollow interior and an end to which the natural blood vessel is capable of being grafted; two pockets also to be located beneath the skin and attached to, yet offset laterally from, the tubular portion, each pocket enclosing a chamber which communicates with the hollow interior of the tubular portion; and at each pocket a port including a grommet to be located over the skin, and also extending through the skin to the pocket, the grommet having an access bore that leads from the exterior surface of the grommet toward the chamber in the pocket, the port at each pocket also having a valve that normally closes the access bore, but is capable if permitting communication between the access bore and the chamber, the valve including a valve seat provided with an aperture at the end of and aligned with access bore in the grommet and also a sealing surface around the aperture; and the valve also including a valve element that moves between a closed position against the sealing surface, wherein it isolates the chamber from the access bore, and an open position, wherein it is separated from the sealing surface.

20. An artificial blood vessel comprising:
   a tubular portion suitable for implanting beneath the skin of a living animal and being formed from a material to which a natural blood vessel will graft, the tubular portion having a lumen;
   a pocket located along and attached to the tubular portion and also being suitable for implanting beneath the skin of a living animal, the pocket projecting laterally beyond the tubular portion and enclosing a chamber into which the lumen of the tubular portion opens, the chamber being wider than the lumen and extending laterally beyond the lumen; and
   a port attached to the pocket and configured to project through the skin of the living animal, the port projecting into the chamber where it is offset from the lumen so that the port does not hinder the flow of blood from the lumen into the chamber, the port including a passage which extends through it and opens into the chamber of the pocket, the port also including a valve element which normally to isolates the passage from the chamber of the pocket, but is displaceable to enable the passage to communicate with the chamber.

* * * * *